US00PP10518P

United States Patent [19]

Smaal

[11] Patent Number: Plant 10,518

[45] Date of Patent: Jul. 21, 1998

[54] BEGONIA PLANT NAMED "ELBA"

[75] Inventor: Andre Smaal, Aalsmeer, Netherlands

[73] Assignee: Begonia Breeders Assoc. B.V., Aalsmeer, Netherlands

[21] Appl. No.: 811,732

[22] Filed: Mar. 6, 1997

[51] Int. Cl.[6] ..... A01H 5/00

[52] U.S. Cl. ..... Plt./87.18

[58] Field of Search ..... Plt./87.17, 87.18

*Primary Examiner*—James R. Feyrer

*Attorney, Agent, or Firm*—C. A. Whealy

[57] ABSTRACT

A distinct cultivar of Begonia plant named 'Elba', characterized by its attractive red fully double flowers that are about 5.5 cm in diameter; resistance to Powdery Mildew under commercial greenhouse conditions; and excellent postproduction longevity.

1 Drawing Sheet

The presnt invention relates to a new and distinct cultivar of Begonia plant, botanically known as *Begonia×hiemalis*, commercially known as Elatior Begonia, and referred to by the cultivar name Elba.

The new cultivar is a product of a planned breeding program conducted by the inventor in Aalsmeer, The Netherlands. The objective of the breeding program is to create new Begonia cultivars having good postproduction longevity and resistance to Powdery Mildew.

The new cultivar originated from a cross made by the inventor in Aalsmeer, The Netherlands, of *Begonia tuberosa* as the female, or seed, parent with *Begonia socotrana* as the male, or pollen, parent.

The cultivar Elba was discovered and selected by the inventor as a flowering plant within the progeny of the stated cross in a controlled environment in Aalsmeer, The Netherlands. The selection of this plant was based on its desirable flower color, uniform, plant habit, numerous flowers, good postproduction longevity and mildew resistance.

Asexual reproduction of the new cultivar by terminal cuttings taken in a controlled environment in Aalsmeer, The Netherlands, has shown that the unique features of this new Begonia are stable and reproduced true to type in successive generations.

The cultivar Elba has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Elba'. These characteristics in combination distinguish 'Elba' as a new and distinct cultivar:

1. Attractive red fully double flowers that are about 5.5 cm in diameter.
2. Resistance to Powdery Mildew under commercial greenhouse conditions.
3. Excellent postproduction longevity.

The accompanying colored photograph illustrates the overall appearance of the new cultivar, showing the colors as true as it is reasonably possible to obtain in colored reproduction of this type. The photograph comprises a top perspective view of a typical flowering plant of 'Elba'. Flower and foliage colors in the photographs may differ from the actual colors due to light reflectance.

In the following description, color references are made to The Royal Horticultural Society Colour Chart except where general terms of ordinary dictionary significance are used. The following observations and measurements describe plants grown in Aalsmeer, The Netherlands, that were flowered in November under commercial practice in a glass-covered greenhouse. Average day temperatures were 20° C. and average night temperatures were 18° C. Assimilation lights provided a maximum light level of 18,000 lux. Measurements and numerical values represent averages for six typical flowering plants.

Botanical classification: *Begonia×hiemalis* cultivar Elba.

Commercial classification: Elatior Begonia.

Parentage:

*Male or pollen parent.*—*Begonia socotrana.*

*Female or seed parent.*—*Begonia tuberosa.*

Propagation:

*Type.*—Terminal cuttings.

*Time to rooting.*—About 14 days with soil temperatures of 23° C.

*Rooting habit.*—Fine, fibrous and well-branched.

Plant description:

*Plant form.*—Upright and rounded potted plant, freely branching with good stem and stem base strength. Flowers are fully double and abundant. Plants flower continuously.

*Growth habit.*—Vigorous. Suitable for 10 to 15-cm containers. Under optimal environmental and cultural conditions, usually 9 weeks are required to produce proportional 13-cm potted plants from terminal cuttings. Vegetative shoots are formed at basal nodes and flowering shoots are formed at upper nodes.

*Plant height.*—About 30 cm.

*Plant width.*—About 25 cm.

*Leaves.*—Arrangement: Simple, alternate. Size: Length: About 14 cm. Width: About 10 cm. Shape: Asymmetrically cordate. Apex: Acute. Base: Cordate, overlapping. Margin: Doubly serrate. Texture: Smooth, shiny, leathery. Color: Young foliage: Upper: 141A. Lower: 138B. Mature foliage: Upper surface: 147A. Lower surface: 138B. Venation: Upper surface: 143C. Lower surface: 138B.

Flower description:

*Flowering habit.*—Fully double flowers arranged in racemes. Many racemes in flower simultaneously. Flowering continuous.

*Natural flowering season.*—Plants will flower earlier and more abundantly if daylength is 12 hours or less. Usually plants start flowering after 7 weeks of start of short day/long night treatments.

*Flowers.*—Shape: Rounded, cupped. Diameter: About 5.5 cm.

*Tepals.*—Arrangement: Rosette. Shape: Flat, rounded with entire margin. Quantity per flower: Usually about 26 per flower. Color: When opening: Upper surface: 52A to 53B. Lower surface: 52A to 47A. Fully opened: Upper surface: 53B. Lower surface: 47A. Texture: Smooth, velvety, glabrous.

*Sepals.*—Arrangement: Two, opposite. Shape: Oval. Color: 138B with red edge.

*Reproductive organs.*—Stamens: None. Pistils: None.

Production longevity:

*Individual flowers.*—Generally 2 to 3 weeks.

*Whole plants.*—About 6 weeks under interior conditions.

Disease resistance: Plants of the cultivar Elba are resistant to Powdery Mildew under greenhouse conditions.

Seed production: Seed production has not been observed as reproductive organs are not formed.

It is claimed:

1. A new and distinct cultivar of Begonia plant named 'Elba', as illustrated and described.

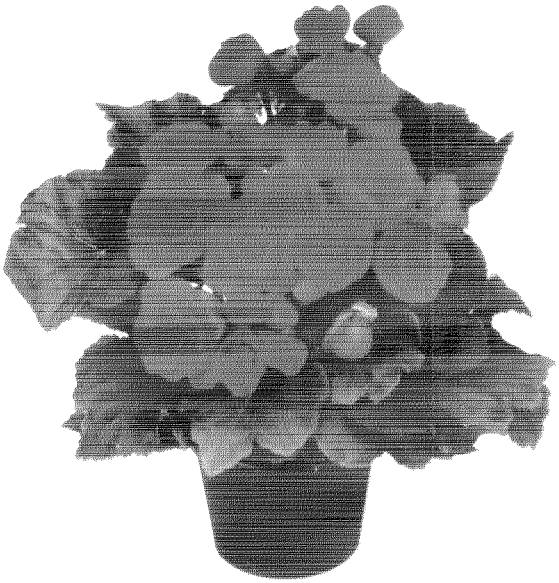

* * * * *